United States Patent [19]

Ichikawa et al.

[11] Patent Number: 4,463,105

[45] Date of Patent: Jul. 31, 1984

[54] PROCESS FOR PRODUCING OXYGEN-CONTAINING HYDROCARBON COMPOUNDS

[75] Inventors: Masaru Ichikawa, Yamato; Kohichi Shikakura, Sagamihara; Kazuhiko Sekizawa, Shinnanyo; Kazuaki Tanaka, Kawasaki, all of Japan

[73] Assignee: Sagami Chemical Research Center, Tokyo, Japan

[21] Appl. No.: 387,265

[22] Filed: Jun. 9, 1982

Related U.S. Application Data

[62] Division of Ser. No. 221,611, Dec. 31, 1980, abandoned.

[30] Foreign Application Priority Data

Apr. 21, 1980 [JP] Japan .................................. 55-51762
Apr. 21, 1980 [JP] Japan .................................. 55-51763

[51] Int. Cl.³ .............................................. C07C 27/06
[52] U.S. Cl. ...................................... 518/716; 518/714
[58] Field of Search ................................ 518/716, 714

[56] References Cited

U.S. PATENT DOCUMENTS 4,116,994  9/1978  Vanniu et al. .
4,199,522  4/1980  Murchison .
4,224,236  9/1980  Wunder et al. .

FOREIGN PATENT DOCUMENTS 0010295  4/1980  European Pat. Off. .

*Primary Examiner*—Howard T. Mars
*Attorney, Agent, or Firm*—Wenderoth, Lind & Ponack

[57] ABSTRACT

In a process for producing an oxygen-containing hydrocarbon compound having 1 or 2 carbon atoms which comprises reacting a gaseous mixture of a carbon oxide and hydrogen in the presence of a hydrogenation catalyst, the improvement wherein said hydrogenation catalyst is a catalyst composition comprising (A) substantially metallic rhodium,
(B) an oxide of a metal selected from the group consisting of metals of Groups, IIa, IIIa, IVa and Va of the periodic table of short form, and
(C) silica or
  (i) substantially metallic rhodium,
  (ii) an element selected from the group consisting of niobium, tantalum, chromium, manganese and rhenium,
  (iii) an oxide of a metal selected from the group consisting of metals of Groups IIIa, IVa and Va of the periodic table of short form, and
  (iv) silica.

10 Claims, No Drawings

PROCESS FOR PRODUCING OXYGEN-CONTAINING HYDROCARBON COMPOUNDS

This application is a division of Ser. No. 221,611, filed Dec. 31, 1980, now abandoned.

This invention relates to a process for producing oxygen-containing hydrocarbon compounds having 1 or 2 carbon atoms by reacting a gaseous mixture composed of carbon oxide and hydrogen in the presence of a hydrogenation catalyst. More specifically, this invention pertains to a process for advantageously producing oxygen-containing hydrocarbon compounds having 1 or 2 carbon atoms, particularly ethanol, from the aforesaid gaseous mixture using a catalyst composition comprising metallic rhodium and a certain metallic oxide as a hydrogenation catalyst.

In recent years, there has been a worldwide scarcity of oil resources, and it is anticipated that a balance between supply and demand of oils will be aggravated in the near future. Naphtha derived from crude oils has become increasingly costly in recent years, and the cost of production of low-boiling olefins, acetic acid, acetaldehyde, ethanol, etc., which are the basic products of the petrochemical industry from naphtha, has tended to increase year by year. Accordingly, there has been an increasing need to develop a process for producing these basic raw materials of the petrochemical industry at low cost from a synthesis gas comprising a mixture of carbon monoxide and hydrogen.

Presently, the synthesis gas is produced industrially by steam-reforming or naphtha and natural gases, but it is expected that in the near future synthesis gases from low-cost carbon resources occurring abundantly throughout the owrld such as heavy oils, coals and oil sands will go into industrial production. The synthesis gas will therefore be an advantageous raw material both in cost and supply.

Extensive investigations have been made heretofore about the production of hydrocarbons or both hydrocarbons and oxygen-containing hydrocarbon compounds from a gaseous mixture of carbon oxide (carbon monoxide or carbon dioxide) and hydrogen (a synthesis gas process or a modified Fischer-Tropsch method). It has been reported, for example, that various oxygen-containing hydrocarbon compounds and hydrocarbons can be synthesized by reacting a synthesis gas comprising carbon monoxide and hydrogen in a ratio of from 4:1 to 1:4 in the presence of a hydrogenation catalyst comprising a metal of the iron group or noble metal group at a temperature of 150° to 450° C. and a pressure of 1 to about 700 atmospheres [F. Fischer, H. Tropsh, Ber., 59, 830, 832, 923 (1926), and H. Pichler, Adv. Catalysis, IV, 271 (1952)]. The product obtained by this method is a mixture of oxygen-containing hydrocarbon compounds and hydrocarbons having 1 to 20 carbon atoms, and this method cannot afford industrially useful oxygen-containing hydrocarbon compounds having low carbon numbers selectively and efficiently.

As a method for synthesizing oxygen-containing hydrocarbon compounds and lower olefins from a synthesis gas, the Hydrocol method comprising performing the reaction at 300° to 350° C. and 20 to 50 atmospheres using a catalyst composed of iron or cobalt supported on magnesium oxide, thorium oxide, etc. [see H. Pichler, Adv. Catalysis IV, 271 (1952)], and the Synthol method involving performing the reaction at 300° to 400° C. and 70 to 250 atmosphere [F. Fischer, H. Tropsch, Brennstoff-Chem., 4, 276 (1923), 5, 201, 217 (1924), 7, 97, 299 (1926), 8, 165 (1927)] have already been known. These methods, however, have poor selectivity. They are advantageous for production of higher olefins, but cannot selectively give olefins having 2 to 4 carbon atoms and oxygen-containing hydrocarbon compounds having 1 or 2 carbon atoms which are useful as industrial materials.

On the other hand, as regards the use of a rhodium catalyst, a method was suggested which comprises contacting a synthesis gas at atmospheric pressure with a rhodium-supported catalyst containing a silica or alumina carrier or a rhodium metal plate to produce methane and not more than 10% of $C_2$-$C_4$ hydrocarbons [see M. A. Vannice, J. Catal., 37, 449 (1975), and B. Sexton, G. A. Somorjai, ibid. 46, 167 (1977)]. Furthermore, about the selective production of oxygen-containing hydrocarbon compounds having low carbon numbers by reaction of a synthetic gas using a rhodium-supported catalyst, there were proposed a method which comprises reacting a synthetic gas at 290° to 325° C. and 35 to 350 atmospheres while maintaining the $CO/H_2$ ratio at much higher than 1 and the flow rate of the reactant gas at $10^3 h^{-1}$ or higher as SV, to produce a mixture of oxygen-containing hydrocarbon compounds having low carbon numbers, especially acetic acid, acetaldehyde and ethanol, in a carbon efficiency, based on the comsumed carbon monoxide, of 50% (Belgian Pat. No. 824822, DT No. 2503233, and Japanese Laid-Open Patent Publication No. 80806/76); and a method which comprises reacting a synthesis gas at a flow rate of at least $10^3 h^{-1}$ under a pressure of 50 to 300 atmospheres using a silica carrier catalyst containing rhodium and iron to produce methanol and ethanol at substantially the same carbon efficiency as in the aforesaid method (see Belgian Patent No. 824823, and Japanese Laid-Open Patent Publication No. 80807/76). These methods give methanol and ethanol in a substantially equimolar ratio, but cause formation of large amounts of methane or hydrocarbons having 2 or more carbon atoms as by-products. At a low CO concentration in the synthesis gas ($CO/H_2 = 1.0$ or less), a low pressure (1 to 50 atmospheres) or a low flow rate (not more than $10^2 h^{-1}$ as SV) which are advantageous conditions for economical industrial processes, by-product hydrocarbons tend to increase further in these methods, and the selectivity for industrially useful oxygen-containing hydrocarbon compounds having 1 to 2 carbon atoms such as ethanol is drastically reduced.

According to an improved method involving use of a catalyst comprising both rhodium and manganese (see Japanese Laid-Open Patent Publication No. 14706/77), an increase in the conversion of CO per unit weight of rhodium is noted, but the addition of manganese can scarcely increase the selectivity for the formation of oxygen-containing hydrocarbon compounds. It has been pointed out that the addition of an excessive amount of manganese rather increases formation of hydrocarbons and reduces the selectivity for the formation of the desirable oxygen-containing hydrocarbon compounds.

A method has also been known for producing a mixture of methanol and ethanol from a synthesis gas by reacting it at 1 to 50 atmospheres and 150° to 300° C. using a catalyst obtained by supporting a rhodium cluster or platinum cluster on an oxide of at least one metal selected from metals of Groups IIab, IIIab and IVab of the periodic table of short form (see Japanese Laid-Open Patent Publications Nos. 41291/79 and 44605/79). Although the catalyst used in this method is highly active, this method still has various difficulties which have to be overcome. For example, catalyst preparation requires the use of a special and expensive noble metal carbonyl cluster compound as a raw material, and includes operation in an inert atmosphere (in vacuum or in an inert gas). The catalyst has a short lifetime under high-temperature and high-pressure conditions which are required for achieving a high conversion, and there is a limit to the operable temperature range for the catalyst.

In view of the prior art techniques discussed above, it has been desired to develop a rhodium-containing catalyst which is suitable for selective production of oxygen-containing hydrocarbon compounds having 1 or 2 carbon atoms, particularly ethanol, at a high carbon efficiency under relatively mild low-pressure reaction conditions. The use of such a rhodium-containing catalyst will provide a new technique which supersedes synthesis of methanol from a synthesis gas or production of ethylene from naphtha.

It is an object of this invention to provide a process for producing oxygen-containing hydrocarbon compounds having 1 or 2 carbon atoms at a high carbon efficiency from a gaseous mixture of carbon oxide and hydrogen using a rhodium-containing catalyst which is relatively inexpensive and is easily available.

Another object of this invention is to provide a process for producing oxygen-containing hydrocarbon compounds having 1 or 2 carbon atoms, especially ethanol, from a gaseous mixture of carbon oxide and hydrogen.

Other objects and advantages of this invention will become apparent from the following description.

It has now been found in accordance with this invention that when a catalyst composition consisting basically of (A) substantially metallic rhodium; (B) an oxide of a metal (to be referred to as a "metal oxide") selected from metals of Groups IIa, IIIa, IVa and Va of the periodic table of short form; and (C) silica is used in the production of oxygen-containing hydrocarbon compounds by reacting a gaseous mixture composed of carbon oxide and hydrogen, the carbon efficiency of the oxygen-containing hydrocarbon compounds having 1 to 2 carbon atoms is markedly improved, and reaches 50% or more. It has also been found that the catalyst composition used in this invention generally has a wide operating temperature range, and exhibits superior catalytic activity at a wide temperature range of from about 100° to about 400° C., and its catalytic activity lasts for an extended period of time even under high-temperature, high-pressure reaction conditions.

Particularly, in accordance with this invention, it has been found that the catalyst composition having a very increased catalytic activity and an extremely high selectivity for ethanol is provided by the joint use of the metallic rhodium and metal oxide with silica. This discovery is surprising in view of the fact that the conjoint use of metallic rhodium and the metal oxide with alumina which is frequently used as a catalyst carrier results in reduced catalytic activity.

According to one aspect of this invention, there is provided a process for producing oxygen-containing hydrocarbon compounds having 1 or 2 carbon atoms which comprises reacting a gaseous mixture consisting of carbon oxide and hydrogen in the presence of a hydrogenation catalyst, said hydrogenation catalyst being a catalyst composition comprising
(A) substantially metallic rhodium;
(B) an oxide of a metal selected from metals of Groups IIa, IIIa, IVa and Va of the periodic table of short form; and
(C) silica.

In the present specification and the appended claims, the term "oxygen-containing hydrocarbon compounds having 1 or 2 carbon atoms" denotes hydrocarbons having 1 or 2 carbon atoms and an oxygen atom, such as methanol, ethanol, formaldehyde, acetaldehyde, formic acid and acetic acid.

The term "carbon oxide" inclusively represents both carbon monoxide (CO) and carbon dioxide ($CO_2$). In the present invention carbon monoxide and carbon dioxide are used either singly or as a mixture. Preferably, the carbon oxide is carbon monoxide.

The "periodic table or short form", as used in the present application, denotes a periodic table of the type described at page 738 of "Encyclopaedia Chimica", Vo. 5 (1951), Kyoritsu Shuppan K.K., Tokyo, Japan. According to this periodic table, Group IIa includes Be, Mg, Ca, Sr, Ba and Ra; Group IIIa, Sc, Y, lanthanide elements and actinide elements; Group IVa, Ti, Zr and Hf; and Group Va, V, Nb and Ta.

The term "carbon efficiency of oxygen-containing hydrocarbon compounds", as used in this application, denotes the percentage of the oxygen-containing hydrocarbon compounds in moles based on the consumed carbon oxide calculated for carbon (on the carbon basis).

The term "selectivity for ethanol", as used in this application, denotes the percentage of ethanol based on the resulting oxygen-containing hydrocarbon compounds calculated for carbon (on the carbon basis).

The metallic oxide used as the component (B) in the catalyst composition in accordance with this invention may be an active catalytic ingredient having the ability to increase synergistically the catalytic activity or metallic rhodium which is a main catalytic ingredient. Or, the metal oxide serves as a part of a carrier for metallic rhodium.

Examples of the metal oxide include magnesium oxide, calcium oxide, beryllium oxide, lanthanum oxide, cerium oxide, neodymium oxide, yttrium oxide, zirconium oxide, titanium oxide, thorium oxide, vanadium oxide, niobium oxide and tantalum oxide. Of these, lanthanum oxide, neodymium oxide, cerium oxide, yttrium oxide, thorium oxide, titanium oxide, zirconium oxide, niobium oxide, and tantalum oxide are preferred. Thorium oxide, titanium oxide, zirconium oxide, niobium oxide and tantalum oxide are especially preferred. These metal oxides can be used either singly or in combination with each other. The catalyst composition according to this invention may comprise silica as a substrate and deposited thereon, metallic rhodium and the metal oxide; or an intimate composite of silica and the metal oxide, and metallic rhodium deposited on the composite.

In the case of the former type, deposition of metallic rhodium and the metal oxide on silica can be performed by any method known per se.

Deposition of metallic rhodium can be performed by any customary method so long as substantially all of the rhodium deposited on the metal oxide is metallic. Advantageously, this can be performed using a simple organic or inorganic salt of rhodium. The "simple salt or rhodium", as referred to herein, means a compound simply containing mono- or dinuclear rhodium element, and is clearly distinct from the cluster compound of rhodium mentioned hereinabove. Specific examples of the simple salt of rhodium include inorganic salts of rhodium such as the chloride, nitrite and carbonate of rhodium, and organic salts of rhodium such as the acetate, oxalate, ethylenediamine complex [$Rh(NH_2C_2H_4NH_2)_3$]$Cl_3$, pyridine complex [$Rh(C_4H_4N)_4Cl_3$], acetylacetonate salt, cyclooctadiene complex, dicyclopentadienyl complex, $\pi$-allyl complex, and allene complex of rhodium.

Deposition of metallic rhodium on the metal oxide with silica and/or the metal oxide-silica composites from these rhodium salts may be performed, for example, by a method which comprises dissolving the rhodium salt in a suitable solvent (for example, water, an alcohol such as methanol or ethanol, an ether such as tetrahydrofuran or dioxane, or a hydrocarbon such as hexane or benzene), impregnating the metal oxide with the resulting solution, removing the solvent, and then heat-treating the impregnated metal oxide in an atmosphere of a reducing gas such as hydrogen gas or synthesis gas under atmospheric or elevated pressures until substantially all of the impregnated rhodium salt is converted to metallic rhodium (for example, at a temperature of about 50° to about 500° C. for about 10 minutes to about 2 days; this reducing treatment can be performed in a reactor prior to the performance of the process of this invention); or chemically reducing the impregnated metal rhodium salt with a reducing agent such as formaldehyde, hydrazine, metal hydrides (e.g., sodium hydride or potassium hydride), metal borohydrides (e.g., sodium borohydride), or complex metal hydrides (e.g., lithium aluminum hydride). As a result, substantially metallic rhodium is supported and combined with the metal oxide with silica and/or the metal oxide-silica composites.

The content of metallic rhodium is not critical, and can be widely varied depending upon the type or shape of the metal oxide used, etc. Generally, it is advantageous that the content of metallic rhodium is about 0.0001 to about 50% by weight, preferably about 0.01 to about 25% by weight, more preferably about 0.1 to about 10% by weight, based on the weight of the catalyst composition.

On the other hand, deposition of the metal oxide can be performed, for example, by dissolving an inorganic or organic metal compound of a metal of Groups IIa, IIIa, IVa and Va of the periodic table of short form in a suitable solvent (for example, water, an alcohol such as methanol or ethanol, an ether such as tetrahydrofuran or dioxane, or a hydrocarbon such as hexane or benzene), impregnating the resulting solution in silica in various forms such as a powder, pellet, granule or lump, removing the solvent, and then heat-treating the impregnated silica in an atmosphere of an oxygen-containing gas (e.g. air), an inert gas (e.g., nitrogen, argon, helium, or carbon dioxide gas), or a reducing gas (e.g., hydrogen or synthesis gas) depending upon the type of the metal compound used until substantially all of the impregnated metal compound is converted to the corresponding metal oxide (for example, heating it at a temperature of about 100° to about 600° C. for about 30 minutes to about 2 days). As a result, the metal oxide can be deposited on silica.

The inorganic or organic metal compound used in the deposition of the metal oxide includes the chlorides, oxynitrates, nitrates, carbonates, hydroxides, acetates, formates, oxalates, silyl ether salts, acetylacetonate salts, polyhydroxystearates, alkoxides, dicyclopentadienyl complexes, $\pi$-allyl complexes, benzyl complexes, and allene complexes of metals of Groups IIa, IIIa, IVa and Va of the periodic table of short form.

Specific examples of these inorganic or organic metal compounds are magnesium chloride ($MgCl_2$), magnesium bromide ($MgBr_2$), magnesium nitrate [$Mg(NO_3)_2$], magnesium hydroxide [$Mg(OH)_2$], magnesium carbonate ($MgCO_3$), magnesium formate [$Mg(HCOO)_2$], magnesium oxalate ($MgC_2O_4.2H_2O$), magnesium per-chlorate [$Mg(ClO_4)_2$], magnesium methoxide [$Mg(OCH_3)_2$], magnesium ethoxide [$Mg(OC_2H_5)_2$], magnesium propoxide [$Mg(OC_3H_7)_2$], magnesium butoxide [$Mg(OC_4H_9)_2$], magnesium methylcarbonate [$Mg(CH_3OCOO)_2$], calcium chloride ($CaCl_2$), calcium bromide ($CaBr_2$), calcium formate [$Ca(HCOO)_2$], calcium oxalate ($CaC_2O_4.2H_2O$), calcium hydroxide [$Ca(OH)_2$], calcium ethoxide [$Ca(OC_2H_5)_2$], calcium butoxide [$Ca(OC_4H_9)_2$], beryllium chloride ($BeCl_2$), beryllium ethoxide [$Be(OC_2H_5)_2$], beryllium formate [$Be(HCOO)_2$], lanthanum chloride ($LaCl_3.3H_2O$), lanthanum nitrate [$La(NO_3)_3.6H_2O$], lanthanum oxalate [$La_2(C_2O_4)_3.nH_2O$], lanthanum acetate [$La(CH_3CO_2)_2.4H_2O$], lanthanum acetylacetonate [$La(C_5H_7O_2)_3.H_2O$], lanthanum carbonate [$La_2(CO_3)_3$], neodymium chloride ($NdCl_3.3H_2O$), neodymium bromide ($NdCl_3$), neodymium nitrate [$Nd(NO_3)_3.3H_2O$], neodymium acetate [$Nd(CH_3COO)_3.nH_2O$], neodymium acetylacetonate [$Nd(C_5H_7O_2)_3.H_2O$], yttrium chloride ($YCl_3$), yttrium chlorate [$Y(ClO_3)_3.9H_2O$], yttrium perchlorate [$Y(ClO_4)_3.9H_2O$], yttrium carbonate [$Y_2(CO_3)_3.3H_2O$], yttrium ammonium carbonate [$(NH_4)Y(CO_3)_2.H_2O$], yttrium formate [$Y(HCOO)_3.2H_2O$], yttrium tertrate [$(Y_2(C_4H_4O_5)_3.nH_2O$], yttrium acetylacetonate [$Y(C_5H_7O_2)_3.H_2O$], cerium chloride ($CeCl_3.7H_2O$) cerium nitrate [$Ce(NO_3)_3.6H_2O$], cerium acetate [$Ce(CH_3CO_2)_3.H_2O$], cerium acetylacetonate [$Ce(C_5H_7O_2)_3$], cerous ammonium nitrate [$Ce(NO_3)_2.2(NH_4NO_3).4H_2O$], ceric ammonium nitrate [$Ce(NO_3)_4.2(NH_4NO_3).nH_2O$], cerium carbonate [$Ce_2(CO_3)_3.8H_2O$], cerium oxalate [$Ce_2(C_2O_4)_3.9H_2O$], zirconium oxynitrate [$ZrO(NO_3)_2.2H_2O$], zirconium nitrate [$Zr(NO_3)_3.6H_2O$], titanium nitrate [$Ti(NO_3)_3.6H_2O$], zirconium oxyacetate [$ZrO(CH_3COO)_3$], titanium oxyacetate [$TiO(CH_3COO)_3$], zirconium oxychloride ($ZrOCl_2$), titanium oxychloride ($TiOCl_2$), zirconium tetrachloride ($ZrCl_4$), titanium tetrachloride ($TiCl_4$), zirconium acetate [$Zr(CH_3COO)_2$], titanium acetate [$Ti(CH_3COO)_2$], zirconium ethoxide [$Zr(OC_2H_5)_4$], titanium ethoxide [$Ti(OC_2H_5)_4$], zirconium isopropoxide [$Zr(iso-C_3H_7O)_4$], titanium isopropoxide [$Ti(iso-C_3H_7O)_4$], zirconium n-propoxide [$Zr(n-C_3H_7O)_4$], titanium n-propoxide [$Ti(n-C_3H_7O)_4$], zirconium butoxide [$Zr(OC_4H_9)_4$], titanium butoxide [$Ti(OC_4H_9)_4$], dicyclopentadienyl zirconium chloride [($\pi$-$C_5H_5)_2ZrCl_2$], dicyclopentadienyl titanium chloride [($\pi$-$C_5H_5)TiCl_2$], dicarbonyldicyclopentadienyl zirconium [($\pi$-$C_5H_5)_2Zr(CO)_2$], dicarbonyldicyclopentadienyl titanium [($\pi$-$C_5H_5)_2Ti(CO)_2$], zirconium acetylacetonate [$Zr(C_5H_7O_2)_4$], titanium acetylacetonate [$Ti(C_5H_7O_2)_4$], thorium nitrate [$Th(NO_3)_4.5H_2O$], thorium acetylacetonate [$Th(C_5H_7O_2)_4$], thorium chloride ($ThCl_4$), thorium acetate [$Th(CH_3COO)_2$], thorium isopropoxide [$Th(iso-C_3H_7O)_4$], thorium n-propoxide [$Th(n-C_3H_7O)$], thorium butoxide [$Th(C_4H_9O)_4$], vanadyl ethoxide [$VO(OC_2H_5)_3$], vanadyl butoxide [VO- (OC$_4$H$_9$)$_3$], vanadyl methoxide [VO(OCH$_3$)$_3$], vanadyl ethoxychloride [VO(OC$_2$H$_5$)$_2$Cl], vanadyl acetylacetone [VO(C$_5$H$_7$O$_2$)$_3$], niobium propoxide [Nb(OC$_3$H$_7$)$_5$], niobium ethoxide [Nb(OC$_2$H$_5$)$_5$], niobium butoxide [Nb(OC$_4$H$_9$)$_5$], niobium acetylacetonate [Nb(C$_5$H$_7$O$_2$)$_3$], vanadocene [($\pi$-C$_5$H$_5$)$_2$V], niobucene [Nb($\pi$-C$_5$H$_5$)$_2$X$_2$] X=Cl, CO, H), tantalum ethoxide [Ta(OC$_2$H$_5$)$_5$], tantalum butoxide [Ta(OC$_4$H$_9$)$_5$], tantalum acetylacetonate [Ta(C$_5$H$_7$O$_2$)$_3$], niobium chloride (NbCl$_5$), tantalum chloride (TaCl$_5$), $\pi$-allyl vanadium carbonyl complex [($\pi$-C$_3$H$_5$)$_2$ V(CO)$_2$], $\pi$-allyl tantalum carbonyl complex [($\pi$-C$_3$H$_5$)$_2$ Ta(CO)$_2$] and benzyl zirconium complex [Zr(CH$_2$C$_6$H$_5$)$_4$].

These metal compounds are generally converted to metal oxides by heat-treatment and/or photo-decomposition in an atmosphere containing an oxygen-containing gas, an inert gas or a reducing gas.

In what condition the metal oxide is deposited on and combined with silica is not clear. It is assumed however that because of a chemical reaction between the metal compound used as a raw material and the hydroxyl group on the surface of silica, at least a part of the deposited metal oxide is in the form of a fixed oxide in which the metal in the metal compound is chemically bonded to a silicon atom through oxygen. It should be understood therefore that the "metal oxide", as used in this invention, also embraces such a fixed oxide.

Deposition of metallic rhodium and deposition of the metal oxide can be performed in various sequences depending upon the depositing conditions. For example, when the deposition of the metal oxide is carried out in an atmosphere containing an oxygen-containing gas or an inert gas, it is generally preferred to perform the deposition of the metal oxide first. When the deposition of the metal oxide is carried out in an atmosphere of a reducing gas, the deposition of metallic rhodium and the deposition of the metal oxide can be performed simultaneously or sequentially in an optional order.

The silica on which the metallic rhodium and the metal oxide are deposited may have a surface area of generally at least 10 m$^2$/g, preferably 10 to 1000 m$^2$/g, more preferably 50 to 500 m$^2$/g. It may assume various ordinary forms as a catalyst substrate, such as a powder, granule, pellet, or lump.

The preferred catalyst composition according to this invention may also be in such a form that metallic rhodium is deposited on a composite of silica and the metal oxide. The composite of silica and the metal oxide can be usually produced by preparing an aqueous solution of a water-soluble silicon compound and a water-soluble metal compound of the type exemplified hereinabove, co-precipitating silicon and the metal in the form of hydroxide from the aqueous solution in a customary manner, separating the co-precipitate, optionally molding it into such a shape as granule or pellet, and then firing it. Deposition of metallic rhodium on the resulting silica-metal composite can be performed by the method described hereinabove.

The resulting catalyst composition comprising metallic rhodium, the metal oxide and silica may contain metallic rhodium in a proportion of generally about 0.0001 to about 50% by weight, preferably about 0.01 to about 25% by weight, more preferably about 0.1 to about 10% by weight, based on the weight of the catalyst composition. The weight ratio of metallic rhodium to the metal oxide is generally from 1:100 to 100:1, preferably from 1:50 to 50:1, more preferably from 1:10 to 10:1, and the weight ratio of the metal oxide to silica is generally from 1000:1 to 1:1000, preferably from 100:1 to 1:100, more preferably from 10:1 to 1:10. The content of silica may be about 0.001 to about 99.9% by weight, preferably about 0.1 to about 98% by weight, more preferably about 1 to about 90% by weight, based on the weight of the catalyst composition.

It has further been found in accordance with this invention that the carbon efficiency of the oxygen-containing hydrocarbon compound having 1 to 2 carbon atoms and the selectivity for ethanol can be further improved by incorporating an element selected from niobium, tantalum, chromium, manganese and rhenium as a sub-main catalyst ingredient into a catalyst composition consisting essentially of metallic rhodium, an oxide of a metal selected from metals of Groups IIIa, IVa and Va of the periodic table of short form, and silica and using the resulting catalyst composition in the reaction of a gaseous mixture of hydrogen and carbon oxide.

Thus, according to another aspect of this invention, there is also provided a process for producing oxygen-containing hydrocarbon compounds having 1 or 2 carbon atoms which comprises reacting a gaseous mixture composed of carbon oxide and hydrogen in the presence of a hydrogenation catalyst, said hydrogenation catalyst being a catalyst composition comprising (i) substantially metallic rhodium;
(ii) an element selected from the group consisting of niobium, tantalum, chromium, manganese and rhenium;
(iii) an oxide of a metal selected from the group consisting of metals of Groups IIIa, IVa and Va of the periodic table of short form; and
(iv) silica.

The catalyst composition used in this process can be prepared in the same way as the aforesaid catalyst composition except that the metal element selected from niobium, tantalum, chromium, manganese and rehenium is additionally deposited on the metal oxide with silica and/or the silica-metal oxide composite.

Deposition of such additional metal element on the metal oxide with silica and/or the silica-metal oxide composite can be performed in the same way as in the deposition of metallic rhodium. For example, it can be performed by dissolving an inorganic or organic salt or alkoxide of the metal element in a suitable solvent (for example, water, an alcohol such as methanol or ethanol, an ether such as tetrahydrofuran or dioxane, or a hydrocarbon such as hexane or benzene), impregnating the resulting solution in the metal oxide with silica and/or the silica-metal oxide composite, removing the solvent, and reducing the impregnated metal salt until substantially all of it is reduced to metallic element as in the case of metallic rhodium.

The inorganic or organic salt or alkoxide of the additional metal element that can be used includes the chlorides, nitrates, carbonates, acetates, oxalates, acetylacetonate salts, dicyclopentadienyl complexes, $\pi$-allyl complexes, allene complexes and alkoxides of the metals. Specific examples include rhenium chloride (ReCl$_5$), rhenium bromide (ReBr$_5$), rhenium carbonyl [(Re$_2$-(CO)$_{10}$], dicyclopentadienyl rhenium hydride [($\pi$-C$_5$H$_5$)$_2$-ReH$_3$], carbonyl dicyclopentadienyl rhenium [($\pi$-C$_5$H$_5$)$_2$-Re(CO)$_2$], rhenium nitrate [Re(NO$_3$)$_5$.6H$_2$O], rhenium acetate [Re(CH$_3$COO)$_5$], ammonium rhenate [(NH$_4$)$_2$Re$_2$O$_4$], niobium chloride (NbCl$_5$), niobium bromide (NbBr$_5$), dicyclopentadienyl niobium hydride [($\pi$-C$_5$H$_5$)$_2$NbH$_3$], $\pi$-allyl niobium

[($\pi$-C$_5$H$_5$)$_4$NB], tantalum chloride (TaCl$_5$), tantalum bromide (TaBr$_5$), dicyclopentadienyl tantalum hydride ($\pi$-C$_5$H$_5$)$_2$TaH$_3$], $\pi$-allyl tantalum [($\pi$-C$_3$H$_5$)$_4$Ta], niobium acetylacetonate [Nb(C$_5$H$_7$O$_2$)$_5$], tantalum acetylacetonate [Ta(C$_5$H$_7$O$_2$)$_5$], manganese chloride (MnCl$_2$.4H$_2$O), manganese acetylacetonate [Mn(C$_5$H$_7$O$_2$)$_2$], manganese acetate [Mn(CH$_3$COO)$_2$.4H$_2$O], manganese nitrate [Mn(NO$_3$)$_2$.6H$_2$O], dicyclopentadienyl manganese [(C$_5$H$_5$)$_2$Mn], chromium chloride (CrCl$_3$, or CrCl$_3$.6H$_2$O), chromium nitrate [Cr(NO$_3$)$_3$.9H$_2$O], chromium acetylacetonate [Cr(C$_5$H$_7$O$_2$)$_3$], dicyclopentadienyl chromium [Cr(C$_5$H$_5$)$_2$], and $\pi$-allyl chromium [($\pi$-C$_3$H$_5$)$_3$Cr]. These metal compounds can be used either singly or in combination with each other.

Deposition of such a metal element can be performed either before, during or after the deposition of metallic rhodium.

The amount of the metal element to be deposited is not critical, and can be varied widely depending upon the type of the metal element, etc. Generally, it is such that the weight ratio of metallic rhodium to the metal element is from 50:1 to 1:50, preferably from 20:1 to 1:20, more preferably from 1:10 to 10:1. The total amount of metallic rhodium and the metal element may be about 0.001 to about 50% by weight, preferably about 0.01 to about 25% by weight, more preferably about 0.1 to about 25% by weight, based on the weight of the catalyst composition.

The reaction of a gaseous mixture of carbon oxide and hydrogen in the presence of the catalyst composition of the various embodiments described hereinabove can be performed in a manner known per se. For example, the reaction can be performed by feeding the catalyst composition into a suitable catalytic reactor such as a closed circulating reactor, a fixed bed type reactor adapted for flowing of a starting gaseous mixture at atmospheric or elevated pressure, a batchwise pressure reactor or a batchwise shaking pressure reactor, and contacting the starting gaseous mixture with the catalyst composition at about 50° to about 450° C. and a space velocity of about 10 to about 10$^6$ liters/liter.hr$^{-1}$, preferably about 10$^2$ to about 10$^5$ liters/liter.hr$^{-1}$, at a temperature of about 100° to about 350° C., and a pressure of about 0.5 to about 350 atmospheres (G), preferably about 1 to about 300 atmospheres (G).

The mole ratio of carbon oxide to hydrogen in the starting gaseous mixture to be fed into the reactor is generally from 20:1 to 1:20, preferably from 1:5 to 5:1, more preferably from 1:2 to 2:1.

Thus, according to the process of this invention, oxygen-containing hydrocarbon compounds having 1 or 2 carbon atoms can be produced with a high carbon efficiency from a gaseous mixture of carbon oxide and hydrogen by using the aforesaid catalyst composition which is easily available commercially and has excellent catalytic activity and selectivity. The process of this invention gives oxygen-containing hydrocarbon compounds containing methanol and/or ethanol as main ingredients. The mixture of methanol and ethanol formed as main ingredients can be easily separated into the constitutents by distillation. Hence, the process of this invention is commercially feasible for production of methanol and ethanol. Moreover, blending of the oxygen-containing hydrocarbon compounds containing methanol and ethanol as main ingredients with a fuel gas gives fuels which may supersede the present fuels from natural resources and are expected to contribute to saving of petroleum resources.

One great advantage of the process of this invention is that ethanol can be produced at a high selectivity when the aforesaid silica-containing metal oxide catalyst composition further includes a metal element selected from niobium, tantalum, chromium, manganese and rhenium in addition to metallic rhodium.

Ethanol can be easily separated from the oxygen-containing hydrocarbon compounds containing a major proportion of ethanol which are obtained by the process of this invention. Hence, the process of this invention is commercially feasible for production of ethanol from a synthesis gas. Moreover, blending of the oxygen-containing hydrocarbon compounds containing ethanol as a main ingredient with a fuel gas or gasoline gives fuels which may supersede the present fuels from natural resources and are expected to contribute to saving of petroleum resources.

The following examples specifically illustrate the present invention. It should be noted however that the present invention is in no way limited by these examples.

The various abbreviations and terms appearing in the following examples have the following meanings.

RG: Reagent grade
SV: Space velocity defined as follows:

$$SV = \frac{\text{Amount of the feed gas (ml/hr)}}{\text{Amount of catalyst (ml)} \times \text{time (hr)}}$$

Feed: Amount of feed gas (ml/hr)
C$_1$: methane
C$_2$: ethane+ethylene
C$_3$: propane+propylene
C$_4$: butane+butene
Tr: trace amount
CE: Carbon efficiency (%) of oxygen-containing hydrocarbon compounds defined as follows:

$$CE = \frac{\text{Moles of methanol} + (\text{moles of ethanol} + \text{moles of acetaldehyde} + \text{moles of acetic acid}) \times 2 + (\text{moles of propanol}) \times 3 + (\text{moles of butanol}) \times 4}{\text{Moles of carbon oxide reacted}} \times 100$$

Selectivity for ethanol (%):

$$\frac{(\text{moles of ethanol formed}) \times 2}{\substack{\text{Moles of the oxygen-containing} \\ \text{hydrocarbon compounds formed} \\ \text{(on carbon basis)}}} \times 100$$

STY: Space time yield
STY of the oxygen-containing hydrocarbon compounds is expressed by the following equation.

$$STY = \frac{\text{Weight of the oxygen-containing hydrocarbon compounds (grams)}}{\text{(weight of the catalyst charged (kg))} \times \text{time (hours)}}$$

EXAMPLE 1

Zirconium oxynitrate dihydrate (2.5 g) was dissolved in 100 ml of distilled water, and 10 g of silica gel pellets (8–10 mesh; a product of Fuji-Davison Chemical Ltd., #57) were added. After dipping, the silica gel pellets were dried by a rotary evaporator, and heat-treated at 500° C. for 15 hours in an electric furnace to decompose zirconium oxynitrate to zirconium oxide (decomposition temperature 230° C.) to obtained zirconium oxide-supported silica gel pellets. Rhodium chloride trihydrate (1.2 g) was dissolved in 100 ml of methanol to form a crimson solution. The zirconium oxide-supported silica pellets were added to the solution, and after dipping, the methanol was evaporated off by a rotary evaporator to obtain a rhodium chloride-supported product. Ten grams of the rhodium chloride-supported product was packed into a flowing-type reactor of Pyrex glass (18 mm in diameter×500 mm in length). Glass beads were placed on the top and bottom of the catalyst layer. While passing a hydrogen gas (1 atmosphere), the temperature was gradually raised from room temperature. Then, the CO-$H_2$ reaction was performed at a total pressure of 1 atmosphere by passing a gaseous mixture of CO and $H_2$ diluted with He (CO:$H_2$:He=20:40:20 ml/min.) through the catalyst layer. At about 150° to 250° C., the amounts of oxygen-containing hydrogen compounds and hydrocarbons formed were measured.

The resulting oxygen-containing hydrocarbon compounds consisted of ethanol as a main ingredient, methanol, acetaldehyde, acetic esters, and traces of propanol and butanol. Every one hour, the off gas was bubbled through 50 ml of distilled water (condenser), and the resulting oxygen-containing hydrocarbon compounds were absorbed and trapped. The products were qualitatively and quantitatively analyzed by an FID gas chromatographic analyzer (Shimazu 7A) using a Porapak Q column (4 m, 200° C., $N_2$ gas carrier). For calibration, acetone was used as an internal standard. Methane, $CO_2$ and CO were analyzed by an active carbon column (1 m, room temperature). $C_2$–$C_4$ hydrocarbons were analyzed qualitatively and quantitatively by a TCD gas chromatographic analyzer (Shimazu 4B) using an alumina-dimethylformamide (supported in an amount of 38% by weight) column. As a result of the overall analysis of the products shown in Table 8, the performance of the present catalyst in the CO-$H_2$ reaction at atmospheric pressure was shown by the conversion of CO, the carbon efficiency (or selectivity) of oxygen-containing hydrocarbon compounds based on the converted CO and the selectivity for ethanol in the oxygen-containing hydrocarbon compounds.

EXAMPLE 2

Rhodium chloride was deposited from its methanol solution on 10 g of silica gel (Davison #57), and the supported product was subjected to reducing treatment in a hydrogen stream ($H_2$:He=40:40, ml/min.) at 1 atmosphere. A solution of 25 g of zirconium oxynitrate dihydrate in 100 ml of methanol was added to the resulting rhodium-silica catalyst. The impregnated catalyst was evaporated in a rotary evaporator to remove the solvent. The resulting catalyst was again packed into a flowing-type reactor, and subjected to reducing treatment in stream of hydrogen at 400° C. and 1 atmosphere. Using the resulting rhodium-zirconia-silica catalyst the CO-$H_2$ reaction was carried out at atmospheric pressure in the same way as in Example 1. The results are shown in Table 1.

EXAMPLE 3

A mixture of 1.2 g of rhodium chloride trihydrate and 2.5 g of zirconium oxynitrate dihydrate was dissolved in 100 ml of methanol, and 10 g of silica gel (Davison #57) was added to the solution. The impregnated silica gel was dried in a rotary evaporator to remove the methanol. The product was subjected to reducing treatment in hydrogen in the same way as in Example 1 to prepare a rhodium-zirconia-silica catalyst. Using 10 g of the resulting catalyst, the CO-$H_2$ reaction was performed at atmospheric pressure. The results are shown in Table 1.

COMPARATIVE EXAMPLE 1

For comparison, a rhodium-silica catalyst was prepared by the same operation as in Example 1 except that 1.2 g of rhodium chloride trihydrate was deposited on 10 g of silica gel (Davison #57) from its methanol solution. Using 10 g of the resulting catalyst, the CO-$H_2$ reaction was carried out under atmospheric pressure in the same way as in Example 1. The results are shown in Table 1.

It is seen from the results given in Table 1 that the silica-supported rhodium catalyst containing zirconium oxide gives a much higher CO conversion and a much higher selectivity for oxygen-containing hydrocarbon compounds, especially ethanol, than does the silica-supported rhodium catalyst not containing zirconium oxide.

TABLE 1

| Catalyst | Example 1 Rh/$ZrO_2$/$SiO_2$ (Rh 0.48 g) $ZrO_2$/$SiO_2$ = 11.4 wt % | | Comparative Example 1 Rh/$SiO_2$ (Rh 0.48 g) | | | Example 2 Rh/$SiO_2$—$ZrO_2$ (Rh 0.48 g) $ZrO_2$/$SiO_2$ = 11.4 wt % | Example 3 Rh—$ZrO_2$—$SiO_2$ (Rh 0.48 g) $ZrO_2$/$SiO_2$ = 11.4 wt % |
|---|---|---|---|---|---|---|---|
| Reaction conditions | | | | | | | |
| SV ($h^{-1}$) | 192 | 192 | 192 | 192 | 192 | 192 | 192 |
| Temperature (°C.) | 200 | 216 | 264 | 278 | 245 | 200 | 200 |
| CO/$H_2$ mole ratio | 0.5 | 0.5 | 0.5 | 0.5 | 0.5 | 0.5 | 0.5 |
| Feed (ml/min.) | 80 | 80 | 80 | 80 | 80 | 80 | 80 |
| Amounts of the products (mmoles/hr) | | | | | | | |
| $CH_3OH$ | 0.09 | 0.04 | — | — | 0.01 | 0.026 | — |
| $CH_3CHO$ | 0.042 | 0.074 | 0.027 | 0.008 | 0.029 | 0.026 | 0.047 |
| $C_2H_5OH$ | 0.363 | 0.470 | — | 0.003 | 0.010 | 0.351 | 0.725 |
| $CH_3COOH$ | — | 0.033 | — | — | — | — | 0.001 |
| $C_1$ | 0.47 | 1.45 | 1.18 | 2.67 | 0.47 | 0.68 | 1.74 |
| $C_2$ | 0.02 | 0.061 | 0.08 | 0.14 | 0.02 | 0.031 | 0.050 |
| $C_3$ | 0.004 | 0.213 | 0.02 | 0.023 | 0.004 | 0.155 | 0.156 |
| $C_4$ | — | — | — | — | — | — | 0.045 |
| $CO_2$ | — | 0.011 | 0.03 | 0.03 | — | 0.042 | 0.024 |
| CO conversion (mole %) | 3.7 | 6.6 | 3.3 | 7.3 | 1.4 | 3.93 | 7.97 |
| CE (%) | 47.3 | 46.4 | 3.7 | 0.8 | 14.9 | 38.5 | 38.5 |

TABLE 1-continued

| Catalyst | Example 1 Rh/ZrO$_2$/SiO$_2$ (Rh 0.48 g) ZrO$_2$/SiO$_2$ = 11.4 wt % | | Comparative Example 1 Rh/SiO$_2$ (Rh 0.48 g) | | | Example 2 Rh/SiO$_2$—ZrO$_2$ (Rh 0.48 g) ZrO$_2$/SiO$_2$ = 11.4 wt % | Example 3 Rh—ZrO$_2$—SiO$_2$ (Rh 0.48 g) ZrO$_2$/SiO$_2$ = 11.4 wt % |
|---|---|---|---|---|---|---|---|
| Ethanol selectivity (%) | 80.8 | 78.7 | −1 | 27 | 22 | 90.0 | 93.8 |
| STY (g/kg cat. hr$^{-1}$) | 2.1 | 2.8 | 0.12 | 0.05 | 0.17 | 1.8 | 3.5 |

EXAMPLE 4

Zirconium oxynitrate dihydrate (2.5 g) and 0.9 g (A), 0.6 g (B) or 0.3 g (C) of rhodium chloride trihydrate were added to methanol. Ten grams of silica gel (Davison #57) was added to the resulting methanol solution. After sufficient dipping, the silica gel was dried by a rotary evaporator to remove the methanol. Each of the resulting products was packed in a flowing-type reactor and subjected to reducing treatment at 400° C. for 15 hours in a hydrogen stream at 1 atmosphere by the same operation as in Example 1. Using each of the catalysts obtained after the reducing treatment, a gaseous mixture of CO and H$_2$ diluted with He was reacted under atmospheric pressure. The reaction products obtained in the steady state at predetermined temperatures were analyzed, and the results are shown in Table 2.

TABLE 2

| | Example 4 | | |
|---|---|---|---|
| | A | B | C |
| Catalyst | Rh—ZrO$_2$/SiO$_2$ (Rh 0.36 g) ZrO$_2$/SiO$_2$ = 11.4 wt % | Rh—ZrO$_2$/SiO$_2$ (Rh 0.24 g) ZrO$_2$/SiO$_2$ = 11.4 wt % | Rh—ZrO$_2$/SiO$_2$ (Rh 0.12 g) ZrO$_2$/SiO$_2$ = 11.4 wt % |
| Reaction conditions | | | |
| SV (hr$^{-1}$) | 192 | 192 | 192 | 192 |
| Temperature (°C.) | 200 | 190 | 201 | 200 |
| CO/H$_2$ mole ratio | 0.5 | 0.5 | 0.5 | 0.5 |
| Feed (ml/min.) | 80 | 80 | 80 | 80 |
| Amount of the products (mmoles/hr) | | | |
| CH$_3$OH | 0.030 | — | 0.023 | 0.020 |
| CH$_3$CHO | 0.048 | 0.031 | 0.025 | 0.019 |
| C$_2$H$_5$OH | 0.521 | 0.270 | 0.249 | 0.099 |
| CH$_3$COOH | 0.019 | 0.001 | — | — |
| C$_1$ | 1.18 | 0.510 | 0.536 | 0.295 |
| C$_2$ | 0.032 | 0.019 | 0.016 | 0.013 |
| C$_3$ | 0.118 | 0.068 | 0.061 | 0.046 |
| C$_4$ | 0.023 | trace | — | — |
| CO$_4$ | 0.086 | trace | — | trace |
| CO conversion | 5.6 | 2.7 | 2.6 | 1.4 |
| CE (%) | 42.8 | 45.0 | 43.3 | 35.8 |
| Ethanol selectivity (%) | 86.4 | 87.5 | 87.2 | 77.3 |
| STY (g/kg catalyst hr$^{-1}$) | 2.7 | 1.4 | 1.3 | 0.60 |

EXAMPLE 5

Zirconium tetra-n-propoxide (6.24 g) was dissolved in 100 ml of n-hexane, and 20 g of silica gel (8–10 mesh; Davison #57) was dipped in the solution. The n-hexane was then evaporated by a rotary evaporator, and the dried product was fired in the air in an electric furnace at 200° C. for 1.5 hours and then at 500° C. for 16 hours to form ZrO$_2$. Ten grams of the resulting zirconium oxide-supported silica pellets where dipped in a solution of 1.2 g of rhodium chloride trihydrate in 100 ml of methanol. The impregnated pellets were dried by a rotary evaporator to remove the solvent to obtain a rhodium chloride catalyst precursor. Ten grams of the catalyst precursor was packed into the same apparatus as used in Example 25, and heat-treated in a stream of hydrogen at 100° C. for 1.5 hours, and then at 400° C. overnight. Using the resulting catalyst, the same CO-H$_2$ reaction as in Example 1 was carried out. The results are shown in Table 3.

EXAMPLE 6

Dicyclopentadienyl zirconium dichloride (2.7 g) was dissolved in 100 ml of tetrahydrofuran, and 10 g of silica gel (8–10 mesh, Davison #57) and dipped in the solution. During the dipping, the solution was refluxed over a warm bath. Then, the impregnated silica gel was dried to remove the tetrahydrofuran. A solution of 1.2 g of rhodium chloride trihydrate in 100 ml of methanol was added to the dried product to deposit rhodium chloride thereon. The solvent was evaporated off to dry the supported catalyst precursor. Ten grams of the catalyst precursor was packed into the same apparatus as used in Example 25, and subjected to reducing treatment in hydrogen stream first at 200° C. for 1 hour and then at 395° C. overnight. Using the resulting catalyst, the CO-H$_2$ reaction was performed in the same way as in Example 1. The results are shown in Table 3.

EXAMPLE 7

Rhodium chloride trihydrate (0.6 g) and 2.5 g of zirconium oxynitrate dihydrate were dissolved in 40 ml of methanol. Ten grams of a silica carrier (a product of Japan Gasoline Chemical Co., Ltd.; surface area 100 m²/g) was dipped in the solution. The impregnated silica carrier was dried to evaporate the solvent. Five grams of the dried product was packed into the same apparatus as used in Example 1, and heat-treated in a stream of nitrogen at 400° C. overnight to decompose and reduce the nitrate. Using the resulting catalyst, the same reaction as in Example 1 was carried out. The results are shown in Table 3.

EXAMPLE 8

Titanium tetraisopropoxide (5.5 g) was dissolved in 100 ml of n-hexane, and 20 g of silica gel (Davison #57) was dipped in the solution. The solvent was evaporated off, and the impreganted silica gel was heat-treated in the air in a drying furnace first at 200° C. for 1.5 hours and then at 500° C. overnight. Ten grams of the $TiO_2$-$SiO_2$ carrier was dipped in a solution of 1.2 g of rhodium chloride trihydrate in 100 ml of methanol to deposit rhodium chloride. The resulting product was dried by a rotary evaporator to remove the methanol, and then heat-treated overnight in the same apparatus as used in Example 1 in a stream of hydrogen at 350° C. The results obtained are shown in Table 3.

with titanium metal and having a size of 40 mm in diameter and 500 mm in length), and subjected to reducing treatment in a stream of hydrogen under 1 atmosphere at 350° C. for 5 hours. Then, a gaseous mixture of CO and $H_2$ under pressure was passed through the catalyst layer. The products at the exit of the reactor were analyzed, and the results are shown in Table 4.

Oxygen-containing hydrocarbon compounds were trapped by bubbling the off gas through two series-connected absorbing towers containing 200 ml of distilled water, and the trapped liquor was quantitatively analyzed by an FID gas-chromatographic analyzer (steam gas-chromatographic analyzer including a cerite column; a product of Okura Rika K.K.) every predetermined period of time. $C_1$-$C_4$ hydrocarbons, CO and $CO_2$ in the off gas were analyzed by a TCD gas-chromatographic analyzer using both an active carbon column (1 m, room temperature, and an $Al_2O_3$-DMF (supported in an amount of 38% by weight) column (4 m, room temperature).

COMPARATIVE EXAMPLE 2

For comparison, the activity of a catalyst prepared by depositing rhodium chloride trihydrate on silica and subjecting the product to reducing treatment in hydrogen at 350° C. was examined in the reaction of a synthesis gas at low to medium pressures. The results are also shown in Table 4.

TABLE 3

| Catalyst | Example 5 Rh/ZrO₂—SiO₂ (Rh 0.48 g) ZrO₂/SiO₂ = 23.5 wt % | | | Example 6 Rh/ZrO₂—SiO₂ (Rh 0.48 g) ZrO₂/SiO₂ = 11.4 wt % | | Example 7 Rh—ZrO₂/SiO₂ (Rh 0.24 g) ZrO₂/SiO₂ = 22.8 wt % | | Example 8 Rh/TiO₂—SiO₂ (Rh 0.48 g) TiO₂/SiO₂ = 15.7 wt % | |
|---|---|---|---|---|---|---|---|---|---|
| Reaction conditions | | | | | | | | | |
| SV (h⁻¹) | 200 | 490 | 1025 | 190 | 190 | 200 | 200 | 190 | 190 |
| Temperature (°C.) | 194 | 194 | 197 | 194 | 190 | 191 | 189 | 181 | 186 |
| CO/H₂ mole ratio | 0.5 | 0.5 | 0.5 | 0.5 | 0.5 | 0.5 | 0.5 | 0.5 | 0.5 |
| Feed (ml/min.) | 83 | 204 | 427 | 79 | 79 | 42 | 42 | 79 | 79 |
| Amounts of the products (mmoles/hr) | | | | | | | | | |
| CH₃OH | 0.023 | 0.032 | 0.071 | 0.012 | 0.010 | 0.017 | 0.011 | 0.057 | 0.037 |
| CH₃CHO | 0.050 | 0.050 | 0.065 | 0.070 | 0.051 | 0.025 | 0.016 | 0.075 | 0.093 |
| C₂H₅OH | 0.835 | 1.055 | 1.257 | 1.064 | 0.853 | 0.326 | 0.281 | 0.710 | 0.909 |
| CH₃COOH | trace | trace | trace | trace | trace | trace | trace | trace | trace |
| C₁ | 1.198 | 1.260 | 1.304 | 1.685 | 1.232 | 0.815 | 0.348 | 1.151 | 2.16 |
| C₂ | 0.067 | 0.052 | 0.067 | 0.121 | 0.094 | 0.029 | 0.024 | 0.033 | 0.063 |
| C₃ | 0.224 | 0.204 | 0.284 | 0.373 | 0.294 | 0.087 | 0.080 | 0.158 | 0.283 |
| C₄ | 0.079 | 0.107 | 0.106 | 0.139 | 0.161 | 0.090 | 0.048 | 0.094 | 0.153 |
| CO₂ | 0.070 | 0.047 | 0.047 | 0.080 | 0.061 | 0.059 | 0.039 | 0.070 | 0.124 |
| CO Conversion (%) | 7.8 | 3.5 | 2.0 | 11.0 | 9.0 | 4.54 | 3.0 | 7.7 | 10.2 |
| CE (%) | 43 | 48 | 49 | 38 | 86 | 52 | 41 | 47.4 | 39.7 |
| Ethanol selectivity (%) | 93 | 94 | 93 | 93 | 94 | 91 | 93 | 81 | 85 |
| STY (g/kg catalyst h⁻¹) | 4.1 | 5.2 | 6.2 | 5.2 | 4.2 | 3.3 | 2.8 | 3.8 | 4.7 |

EXAMPLE 9

Ten grams (25 ml) of the catalyst used in Example 1 was packed in a stainless steel pressure reactor (lined

TABLE 4

| Catalyst | Example 9 Rh/ZrO₂—SiO₂ (Rh 0.48 g, ZrO₂/SiO₂ = 11.4 wt %) | | | | | | Comparative Example 2 Rh/SiO₂ (Rh 0.48 g) | |
|---|---|---|---|---|---|---|---|---|
| CO Conversion (mole %) | 1.1 | 2.2 | 2.4 | 1.5 | 1.7 | 1.5 | 3.7 | 1.1 |
| Reaction conditions | | | | | | | | |
| Gas pressure (kg/cm²) | 20 | 20 | 20 | 20 | 40 | 40 | 20 | 20 |
| Temperature (°C.) | 240 | 240 | 220 | 220 | 240 | 240 | 292 | 282 |
| CO/H₂ mole ratio | 0.5 | 0.5 | 0.5 | 0.5 | 0.5 | 0.5 | 0.5 | 0.5 |
| Feed (ml/min.) | 2400 | 800 | 800 | 1600 | 1600 | 2400 | 800 | 800 |
| SV (h⁻¹) | 5760 | 1920 | 1920 | 3840 | 3840 | 5760 | 960 | 960 |
| Amounts of the products (mmoles/hr) | | | | | | | | |
| CH₃OH | 2.75 | 0.85 | 1.23 | 2.51 | 3.16 | 4.42 | 0.04 | 0.04 |
| CH₃CHO | 0.58 | 0.36 | 0.47 | 0.57 | 0.78 | 1.20 | 1.59 | 0.87 |
| C₂H₅OH | 5.32 | 3.08 | 3.42 | 5.07 | 5.11 | 7.00 | 0.91 | 0.24 |
| CH₃COOH | 1.00 | 1.20 | 1.41 | 1.26 | 1.67 | 2.53 | trace | trace |

TABLE 4-continued

| Catalyst | Example 9 Rh/ZrO$_2$—SiO$_2$ (Rh 0.48 g, ZrO$_2$/SiO$_2$ = 11.4 wt %) | | | | | | Comparative Example 2 Rh/SiO$_2$ (Rh 0.48 g) | |
|---|---|---|---|---|---|---|---|---|
| C$_3$H$_7$OH | trace | trace | trace | trace | trace | trace | trace | trace |
| C$_4$H$_9$OH | trace | trace | trace | trace | trace | trace | trace | trace |
| C$_1$ | 3.23 | 3.47 | 3.13 | 2.82 | 3.25 | 3.80 | 18.2 | 3.67 |
| C$_2$ | 0.085 | 0.083 | 0.110 | 0.117 | 0.099 | 0.067 | 2.70 | 0.89 |
| C$_3$ | 0.128 | 0.114 | 0.106 | 0.114 | 0.116 | 0.114 | 2.69 | 1.92 |
| C$_4$ | trace | trace | trace | trace | trace | trace | 0.12 | 1.04 |
| CO$_2$ | 0.115 | trace | 0.060 | 0.117 | 0.119 | 0.269 | — | — |
| CE (%) | 80.7 | 71.2 | 76.0 | 82.2 | 82.3 | 84.9 | 11.2 | 12.8 |
| STY (g/kg of catalyst hr$^{-1}$) | 42.1 | 26.6 | 30.4 | 41.6 | 47.3 | 67.4 | 11.5 | 5.2 |

EXAMPLE 10

Using 10 g of the catalyst (Rh/ZrO$_2$-SiO$_2$) prepared in Example 25, a gaseous mixture of CO, CO$_2$ and H$_2$ under a total pressure of 1 atmosphere was reacted. The amounts of the products formed per hour are shown in Table 5.

TABLE 5

| Catalyst | Rh/ZrO$_2$—SiO$_2$ | |
|---|---|---|
| Temperature (°C.) | 200 | 200 |
| Feed composition (ml/min.) | | |
| CO | 20 | 15 |
| H$_2$ | 40 | 40 |
| He | 20 | 20 |
| CO$_2$ | 5 | 5 |
| Amounts of the products (mmole/hr) | | |
| CH$_3$OH | 0.08 | 0.07 |
| CH$_3$CHO | 0.041 | 0.038 |
| C$_2$H$_5$OH | 0.361 | 0.340 |
| CH$_3$COOH | trace | trace |
| C$_1$ | 0.48 | 0.30 |
| C$_2$ | 0.02 | 0.02 |
| C$_3$ | 0.04 | 0.03 |
| C$_4$ | trace | trace |
| CE (%) | 58.0 | 61.8 |

EXAMPLE 11 AND COMPARATIVE EXAMPLE 3

Thorium acetylacetonate (12 g) was dissolved in 200 ml of benzene, and 20 g of silica gel (Davison #57) heat-treated in vacuum at 300° C. for 3 hours was dipped in the solution by standing overnight at room temperature. The solvent was evaporated off by using a rotary evaporator, and the dried product was heated in the air first at 200° C. for 2 hours and then at 500° C. for 24 hours to obtain thorium oxide-supported silica gel.

Ten grams of the thorium oxide-supported silica gel was dipped in a solution of 1.2 g of rhodium chloride trihydrate in 100 ml of methanol. The methanol was evaporated off to obtain a rhodium-supported catalyst. Ten grams of the catalyst was packed into a flow-type reactor of Pyrex glass (20 mm in diameter and 450 mm in length), and subjected to reducing treatment in hydrogen at 400° C. overnight after gradually raising the temperature from room temperature.

A gaseous mixture of CO and H$_2$ diluted with He was passed under a total pressure of 1 atmosphere through the resulting catalyst layer, and reacted. The CO:H$_2$:He mole ratio of the gaseous mixture was 1:2:1, and the reaction temperature was varied between 180° and 250° C. The reaction products were quantitatively and qualitatively analyzed in the same way as in Example 1. The results are shown in Table 6.

For comparison, a catalyst was prepared in the same way as in Example 11 except that 1.2 g of rhodium chloride trihydrate was deposited on 10 g of silica gel (Davison #57) from its methanol solution. Using 10 g of the resulting catalyst, the CO-H$_2$ reaction was carried out under atmospheric pressure, and the results are shown in Table 6.

EXAMPLE 12

Thorium nitrate tetrahydrate (8.05 g) was dissolved in 100 ml of distilled water, and 15 g of silica gel (Davison #57) heat-treated in vaccum at 300° C. for 2 hours was dipped in the solution. The solvent was evaporated off by a rotary evaporator, and the dried product was heated overnight at 500° C. in an electric furnace. Ten grams of the resulting thorium oxide-supported silica gel was dipped in a solution of 1.2 g of rhodium chloride trihydrate in 100 ml of methanol. The methanol was evaporated off. Ten grams of therresulting catalyst was packed into the same apparatus as in Example 11, and subjected to reducing treatment in a stream of hydrogen at 370° C. overnight after raising the temperature from room temperature. Using the resulting catalyst, the same reaction as in Example 11 was carried out. The results are shown in Table 6.

TABLE 6

| | | Reaction conditions | | | | | Composition of the product | | | |
|---|---|---|---|---|---|---|---|---|---|---|
| | | Feed composition (ml/min.) | | | SV | Temperature | Oxygen-containing hydrocarbon compounds (mmoles/hr) | | | |
| Example | Catalyst | H$_2$ | CO | He | (hr$^{-1}$) | (°C.) | CH$_3$OH | C$_2$H$_5$OH | CH$_3$CHO | CH$_3$COOCH$_3$ |
| 11 | Rh—ThO$_2$—SiO$_2$ | 40 | 20 | 20 | 200 | 199 | 0.023 | 0.842 | 0.025 | — |
| | (Rh 0.48 g) | 40 | 20 | 20 | 200 | 190 | 0.009 | 0.383 | 0.023 | |
| | ThO$_2$/SiO$_2$ = 25 | 40 | 20 | 20 | 200 | 221 | 0.015 | 0.783 | 0.076 | |
| | wt % | 200 | 100 | 100 | 1000 | 224 | 0.020 | 1.131 | 0.078 | — |
| 12 | Rh—ThO$_2$—SiO$_2$ | 41.7 | 20.0 | 19.5 | 200 | 200 | 0.013 | 0.289 | 0.019 | — |
| | (Rh 0.48 g) | 40 | 20 | 20 | 200 | 217 | 0.016 | 0.232 | 0.032 | |
| | ThO$_2$/SiO$_2$ = 26 wt % | 200 | 100 | 100 | 1000 | 217 | 0.015 | 0.318 | 0.045 | — |
| Comparative Example 3 | Rh—SiO$_2$ (Rh 0.48 g) | 40 | 20 | 20 | 192 | 264 | — | — | 0.027 | — |
| | | 40 | 20 | 20 | 192 | 278 | — | 0.003 | 0.008 | — |
| | | 40 | 20 | 20 | 192 | 245 | 0.01 | 0.010 | 0.029 | — |

TABLE 6-continued

| | Composition of the product | | | | | | | | | |
|---|---|---|---|---|---|---|---|---|---|---|
| | Oxygen-containing hydrocarbon compounds (mmoles/hr) | | Hydrocarbons (mmoles/hour) | | | | | CO conversion (mole %) | CE (%) | Ethanol selectivity (%) |
| Example | $CH_3COOC_2H_5$ | $n-C_3H_7OH$ | $C_1$ | $C_2$ | $C_3$ | $C_4$ | $CO_2$ | | | |
| 11 | — | — | 0.955 | 0.045 | 0.116 | 0.056 | 0.081 | 6.8 | 50.8 | 95.8 |
| | 0.024 | — | 0.332 | 0.018 | 0.048 | 0.018 | 0.065 | 3.0 | 58.6 | 88.8 |
| | 0.065 | 0.011 | 2.445 | 0.127 | 0.263 | 0.121 | 0.170 | 11.9 | 32.8 | 83.7 |
| | 0.021 | 0.031 | 3.33 | 0.15 | 0.317 | 0.137 | 0.071 | 29 | 33.5 | 88.1 |
| 12 | — | — | 0.436 | 0.032 | 0.043 | 0.009 | 0.082 | 2.6 | 45.7 | 91.9 |
| | — | — | 0.863 | 0.061 | 0.068 | 0.016 | 0.095 | 3.5 | 28.8 | 85.3 |
| | — | — | 0.841 | 0.048 | 0.057 | — | 0.065 | 0.67 | 38.3 | 85.8 |
| Comparative Example 3 | — | — | 1.18 | 0.08 | 0.02 | — | 0.03 | 3.3 | 3.7 | −1 |
| | — | — | 2.67 | 0.14 | 0.023 | — | 0.03 | 7.3 | 0.8 | 27 |
| | — | — | 0.47 | 0.02 | 0.004 | — | — | 1.4 | 14.9 | 22 |

EXAMPLE 13

Twenty grams of silica gel (Davison #57) heat-treated in vacuum at 300° C. for 3 hours was dipped in a solution of 5.5 g of vanadyl tritertiary butoxide [VO(O-tert-$C_4H_9$)$_3$] in 100 ml of n-hexane. The solvent was evaporated off, and the dried product was heated in the air in an electric furnace at 200° C. for 1.5 hours and at 500° C. for a day and night to obtain red vanadium oxide-supported silica gel. Ten gram of the resulting silica carrier was added to a solution of 1.2 g of rhodium chloride trihydrate in 100 ml of methanol to support rhodium chloride. The methanol was evaporated off, and 10 g of the resulting product was subjected to reducing treatment in the same apparatus and by the same method as in Example 11 at 310° C. Using the resulting catalyst, the same reaction as in Example 11 was carried out. The results are shown in Table 7.

EXAMPLE 14

Twenty grams of silica gel (Davison #57) heat-treated in vacuum at 300° C. for 2 hours was dipped in a solution of 10.42 g of tantalum penta-n-butoxide [Ta(O-n-$C_4H_9$)$_5$] in 120 ml of n-hexane. The n-hexane was evaporated off, and the dried product was heat-treated in an electric furnace at 200° C. for 1 hour, and then at 500° C. overnight to obtain tantalum oxide-supported silica gel.

Ten grams of the tantalum oxide-supported silica gel was dipped in a solution of 1.2 g of rhodium chloride trihydrate in 100 ml of methanol to deposit rhodium chloride. The methanol was evaporated off, and 10 g of the dried product was subjected to reducing treatment in the same way as in Example 11. Using the resulting catalyst, the same reaction as in Example 11 was carried out. The results are shown in Table 7.

EXAMPLE 15

Twenty grams of silica gel (Davison #57) heat-treated in vacuum at 300° C. for 2 hours was added to a solution of 8.60 g of niobium penta-n-butoxide [Nb(O-n-$C_4H_9$)$_5$] in 100 ml of n-hexane. The n-hexane was evaporated off, and the dried product was heat-treated in an electric furnace at 200° C. for 1 hour and then at 500° C. overnight. Ten grams of the resulting niobium oxide-supported silica gel was added to a solution of 1.2 g of rhodium chloride trihydrate in 100 ml of methanol to support rhodium chloride. The product was subjected to reducing treatment in the same way as in Example 11. Using the resulting catalyst, the same reaction as in Example 11 was carried out. The results are shown in Table 7.

EXAMPLE 16

Five grams of vanadyl acetylacetonate [VO($C_5H_7O_2$)$_2$] was dissolved in 200 ml of benzene, and 20 g of silica gel (Davison #57) heat-treated in vacuum at 280° C. for 3 hours was added to the solution. The benzene was evaporated off, and the dried product was heated in the air in an electric furnace first at 200° C. for 2 hours and then at 500° C. overnight to obtain vanadium oxide-supported silica gel. Ten grams of the vanadium oxide-supported silica gel was dipped in a solution of 1.2 g of rhodium chloride trihydrate in 100 ml of methanol. The methanol was evaporated off, and 10 g of the dried product was packed into the same apparatus as in Example 11, and subjected to reducing treatment in a stream of hydrogen at 120° C. for 1 hour, and after gradually raising the temperature, at 360° C. overnight. Using the resulting catalyst, the same reaction as in Example 11 was carried out. The results are shown in Table 7.

TABLE 7

| | | Reaction conditions | | | | | Composition of the product | | | |
|---|---|---|---|---|---|---|---|---|---|---|
| | | Feed composition (ml/min.) | | | SV | Temperature | Oxygen-containing hydrocarbon compounds (mmoles/hr) | | | |
| Example | Catalyst | $H_2$ | CO | HO | $(hr^{-1})$ | (°C.) | $CH_3OH$ | $C_2H_5OH$ | $CH_3CHO$ | $CH_3COOCH_3$ |
| 13 | Rh—$V_2O_5$—$SiO_2$ | 40 | 20 | 20 | 200 | 197 | 0.080 | 0.537 | 0.033 | — |
| | (Rh 0.48 g) | 200 | 100 | 100 | 1000 | 199 | 0.079 | 0.666 | 0.045 | — |
| | $V_2O_5/SiO_2$ = 8.8 wt % | 40 | 20 | 20 | 200 | 183 | 0.025 | 0.300 | 0.018 | — |
| 14 | Rh—$Ta_2O_5$—$SiO_2$ | 40 | 20 | 20 | 200 | 196 | 0.126 | 0.864 | 0.067 | 0.011 |
| | (Rh 0.48 g) | 40 | 20 | 20 | 200 | 189 | 0.054 | 0.680 | 0.051 | 0.007 |
| | $Ta_2O_5/SiO_2$ = 21 | 40 | 20 | 20 | 200 | 178 | 0.034 | 0.497 | 0.035 | 0.004 |
| | wt % | 100 | 50 | 50 | 500 | 194 | 0.049 | 0.902 | 0.077 | 0.003 |
| 15 | Rh—$Nb_2O_5$—$SiO_2$ | 40 | 20 | 20 | 200 | 200 | 0.005 | 0.441 | 0.102 | — |
| | (Rh 0.48 g) | 40 | 20 | 20 | 200 | 187 | — | 0.232 | 0.062 | — |
| | $NbO_5/SiO_2$ = 12 wt % | | | | | | | | | |
| 16 | Rh—$V_2O_5$—$SiO_2$ | 40 | 20 | 20 | 200 | 199 | 0.039 | 0.347 | 0.027 | — |

TABLE 7-continued

| | | | | | | | | | |
|---|---|---|---|---|---|---|---|---|---|
| (Rh 0.48 g) V$_2$O$_5$/SiO$_2$ = 8.6 wt % | 200 | 100 | 100 | 1000 | 202 | 0.046 | 0.421 | 0.029 | — |

| | Composition of the product | | | | | | | | |
|---|---|---|---|---|---|---|---|---|---|
| | Oxygen-containing hydrocarbon compounds (mmoles/hr) | | Hydrocarbons (mmoles/hr) | | | | | CO conversion | CE | Ethanol selectivity |
| Example | CH$_3$COOC$_2$H$_5$ | n-C$_3$H$_7$OH | C$_1$ | C$_2$ | C$_3$ | C$_4$ | CO$_2$ | (mole %) | (%) | (%) |
| 13 | 0.015 | 0.013 | 0.964 | 0.187 | 0.164 | 0.112 | 0.34 | 7.5 | 34.3 | 84.2 |
|    | trace | 0.019 | 1.10  | 0.226 | 0.244 | 0.139 | 0.49 | 1.7 | 31.8 | 85.5 |
|    | 0.006 | 0.005 | 0.352 | 0.061 | 0.075 | 0.022 | 0.31 | 3.3 | 38.9 | 87.4 |
| 14 | 0.070 | —     | 2.02  | 0.137 | 0.511 | 0.278 | 0.120 | 13.4 | 31.3 | 81.2 |
|    | 0.087 | —     | 1.157 | 0.082 | 0.307 | 0.161 | 0.097 | 8.8 | 38.7 | 81.4 |
|    | 0.063 | —     | 0.572 | 0.025 | 0.145 | 0.085 | 0.025 | 5.3 | 48.9 | 82.2 |
|    | 0.068 | 0.025 | 1.029 | 0.061 | 0.233 | 0.082 | 0.053 | 3.4 | 51.5 | 82.1 |
| 15 | 0.087 | 0.025 | 1.414 | 0.243 | 0.459 | 0.162 | 0.533 | 11.2 | 25.4 | 69.7 |
|    | 0.049 | 0.003 | 0.432 | 0.090 | 0.179 | 0.110 | 0.236 | 4.9 | 30.2 | 71.1 |
| 16 | 0.014 | 0.021 | 0.662 | 0.179 | 0.185 | 0.123 | 0.320 | 5.7 | 30.5 | 79.6 |
|    | —     | 0.023 | 0.826 | 0.201 | 0.234 | 0.116 | 0.272 | 1.4 | 28.2 | 80.6 |

EXAMPLE 17

A flowing-type pressure reactor made of stainless steel and lined with titanium (40 mm in diameter and 500 mm in length) was filled with 5.0 g (12 ml) of the catalyst used in Example 11. The catalyst was subjected to reducing treatment in a stream of hydrogen under 1 atmosphere at 350° C. for 15 hours, and a gaseous mixture of CO and H$_2$ under pressure was passed through the catalyst layer and reacted. The products at the exit of the reactor were analyzed, and the results are shown in Table 8.

TABLE 8

| | Example 17 | | | |
|---|---|---|---|---|
| Catalyst | Rh—ThO$_2$—SiO$_2$ | | | |
| Reaction conditions | | | | |
| Pressure (kg/cm$^2$) | 20 | 20 | 40 | 60 |
| Temperature (°C.) | 230 | 250 | 260 | 270 |
| CO/H$_2$ mole ratio | 0.5 | 0.5 | 0.5 | 0.5 |
| SV (h$^{-1}$) | 3840 | 7680 | 7680 | 11520 |
| Feed (ml/min.) | 800 | 1600 | 1600 | 2400 |
| Composition of the products (mmoles/hr) | | | | |
| CH$_3$OH | 1.45 | 3.71 | 6.67 | 20.6 |
| CH$_3$CHO | 0.17 | 0.31 | 0.45 | 0.85 |
| C$_2$H$_5$OH | 1.50 | 3.65 | 6.83 | 18.0 |
| CH$_3$COOH | 0.44 | 1.05 | 1.71 | 3.09 |
| n-C$_3$H$_7$OH | 0.060 | 0.12 | 0.18 | 0.311 |
| n-C$_4$H$_9$OH | trace | trace | trace | trace |
| C$_1$ | 1.15 | 3.04 | 4.08 | 9.62 |
| C$_2$ | 0.028 | 0.072 | 0.10 | 0.175 |
| C$_3$ | 0.054 | 0.079 | 0.10 | 0.166 |
| C$_4$ | trace | trace | trace | trace |
| CO$_2$ | 0.055 | 0.214 | 0.203 | 0.395 |
| CO conversion (%) | 1.1 | 1.4 | 2.3 | 3.9 |
| CE (%) | 80.1 | 79.5 | 84.0 | 85.7 |
| STY | 30 | 74 | 132 | 308 |

EXAMPLE 18

Zirconium oxynitrate dihydrate (2.5 g) was dissolved in 100 ml of water, and 10 g of silica gel pellets (Davison #57; 8-10 mesh) were added to the solution. The impregnated silica gel pellets were heat-treated in the air at 500° C. for a day and night in an electric furnace to obtain zirconium oxide-containing carrier. The product was dipped in a solution of 1.2 g of rhodium chloride trihydrate and 0.133 g of niobium chloride in 20 ml of ethanol. The ethanol was removed by a rotary evaporator, and 10 g of the RhCl$_3$-NbCl$_5$ supported product was packed into a flow-type reactor of Pyrex glass (18 mm in diameter and 500 mm in length). The temperature was gradually raised from room temperature while passing a helium-diluted hydrogen gas (1 atm., H$_2$:He=40:40, ml/min.) through the reactor, and finally the RhCl$_3$-NbCl$_5$ supported product was subjected to reducing treatment in hydrogen at 400° C. overnight.

Using the resulting catalyst, a gaseous mixture consisting of CO, H$_2$ and He (CO:H$_2$:He=20:40:20, ml/min.) was reacted under a total pressure of 1 atm. The amounts of oxygen-containing hydrocarbon compounds and hydrocarbons formed at about 150° to 250° C. were analyzed by the same method as in Example 11. The results are shown in Table 9.

COMPARATIVE EXAMPLE 4

Rhodium chloride trihydrate (1.2 g) was deposited from its methanol solution on 10 g of silica gel (Davison #57), and reduced with hydrogen at 400° C. by the same operation as in Example 18. Using 10 g of the resulting catalyst, the CO-H$_2$ reaction was carried out under atmospheric pressure in the same way as in Example 18. The results are also shown in Table 9.

TABLE 9

| | Example 18 | | | | | | Comparative Example 4 | | |
|---|---|---|---|---|---|---|---|---|---|
| | Rh—Nb/ZrO$_2$—SiO$_2$ | | | | | | Rh/SiO$_2$ | | |
| Catalyst | (Rh 0.48 g, Nb 0.058 g) ZrO$_2$/SiO$_2$ = 11.4 wt % | | | | | | (Rh 0.48 g) | | |
| Reaction conditions | | | | | | | | | |
| SV (hr$^{-1}$) | 192 | 192 | 192 | 192 | 192 | 192 | 192 | | |
| Temperature (°C.) | 200 | 190 | 200 | 185 | 264 | 278 | 245 | | |
| CO/H$_2$ mole ratio | 0.5 | 0.5 | 0.5 | 0.5 | 0.5 | 0.5 | 0.5 | | |
| Feed (ml/min) | 80 | 80 | 80 | 80 | 80 | 80 | 80 | | |
| Amounts of the products (mmoles/hr) | | | | | | | | | |
| CH$_3$OH | 0.026 | 0.024 | 0.031 | 0.009 | — | — | 0.01 | | |
| CH$_3$CHO | 0.094 | 0.062 | 0.077 | 0.042 | 0.027 | 0.008 | 0.029 | | |
| C$_2$H$_5$OH | 0.743 | 0.471 | 0.758 | 0.384 | — | 0.003 | 0.010 | | |
| CH$_3$COOH | 0.115 | 0.084 | 0.109 | 0.074 | — | — | — | | |
| C$_1$ | 2.260 | 0.794 | 1.940 | 0.074 | 1.18 | 2.67 | 0.47 | | |
| C$_2$ | 0.098 | 0.042 | 0.079 | 0.030 | 0.08 | 0.14 | 0.02 | | |
| C$_3$ | 0.251 | 0.114 | 0.190 | 0.030 | 0.02 | 0.023 | 0.004 | | |
| C$_4$ | 0.034 | trace | 0.022 | trace | trace | trace | trace | | |
| CO$_2$ | 0.180 | 0.085 | 0.245 | 0.056 | 0.03 | 0.03 | trace | | |
| CO conversion (mole %) | 10.4 | 5.0 | 9.6 | 4.1 | 3.3 | 7.3 | 1.4 | | |
| CE (%) | 37.1 | 49.1 | 39.0 | 47.3 | 3.7 | 0.8 | 14.9 | | |
| Ethanol | 77.0 | 75.0 | 79.0 | 76.1 | 0 | 27 | 22 | | |

TABLE 9-continued

| Catalyst | Example 18 Rh—Nb/ZrO$_2$—SiO$_2$ (Rh 0.48 g, Nb 0.058 g) ZrO$_2$/SiO$_2$ = 11.4 wt % | | | | Comparative Example 4 Rh/SiO$_2$ (Rh 0.48 g) | | |
|---|---|---|---|---|---|---|---|
| selectivity (%) | | | | | | | |
| STY | 4.4 | 3.0 | 4.6 | 2.4 | 0.12 | 0.05 | 0.17 |

EXAMPLE 19

Zirconium oxynitrate dihydrate (2.5 g) was deposited on 10 g of silica gel (Davison #57), and heat-decomposed at 500° C. in an electric furnace to obtain a carrier containing zirconium. The carrier was dipped in a solution of 1.2 g of rhodium chloride trihydrate and 0.314 g of rhenium chloride in 100 ml of methanol. The solvent was removed by a rotary evaporator, and 10 g of the resulting product was packed into a flowing-type reactor, and subjected to reducing treatment in hydrogen at 400° C. by the same operation as in Example 18. Using the resulting catalyst, the CO-H$_2$ reaction was carried out under atmospheric pressure in the same way as in Example 18. The results are shown in Table 10.

EXAMPLE 20

Rhodium chloride trihydrate (1.2 g), zirconium oxynitrate dihyrate (2.5 g) and rhenium chloride (0.59 g) were successively dissolved in 100 ml of methanol. Ten grams of silica gel (Davison #57) was fully dipped in the resulting solution. The methanol was removed by a rotary evaporator. The resulting product was subjected to reducing treatment in hydrogen by the same operation as in Example 18. Using 10 g of the resulting catalyst, the CO-H$_2$ reaction was carried out under atmospheric pressure. The results are shown in Table 10.

EXAMPLE 21

Ten grams of the same zirconium-containing carrier as used in Example 18 [prepared from 2.5 g of ZrO(NO$_3$)$_2$.2H$_2$O and 10 g of SiO$_2$ (Davison #57) was fully dipped in a solution of 1.2 g of rhodium chloride trihydrate and 0.48 g of tantalum chloride in 20 ml of ethanol. The ethanol was removed by a rotary evaporator. The dried product was packed into a flowing-type reactor, and subjected to reducing treatment in hydrogen at 400° C. by the same operation as in Example 18. Using 10 g of the resulting catalyst, the CO-H$_2$ reaction was carried out under atmospheric pressure. The results are shown in Table 10.

EXAMPLE 22

The procedure of Example 2 was repeated except that the amount of tantalum chloride was changed to 0.78 g. The results are also shown in Table 10.

TABLE 10

| Example | Catalyst | Reaction conditions SV (h$^{-1}$) | Temperature (°C.) | CO/H$_2$ mole ratio | Feed (ml/min.) | Amounts of the products (mmoles/hr) CH$_3$OH | CH$_3$CHC | C$_2$H$_5$CH | CH$_3$COOH | C$_1$ |
|---|---|---|---|---|---|---|---|---|---|---|
| 19 | Rh—Re/ZrO$_2$—SiO$_2$ | 192 | 196 | 0.5 | 80 | 0.046 | trace | 0.550 | trace | 0.567 |
|  | (Rh 0.48 g, Re 0.16 g) | 192 | 211 | 0.5 | 80 | 0.089 | trace | 0.621 | trace | 1.500 |
|  | ZrO$_2$/SiO$_2$ = 11.4 wt % | | | | | | | | | |
| 20 | Rh—Re—ZrO$_2$/SiO$_2$ | 192 | 200 | 0.5 | 80 | 0.097 | 0.084 | 1.051 | trace | 1.788 |
|  | (Rh 0.48 g, Re 0.30 g) | 192 | 190 | 0.5 | 80 | 0.064 | 0.032 | 0.329 | 0.011 | 0.562 |
|  | ZrO$_2$/SiO$_2$ = 11.4 wt % | | | | | | | | | |
| 21 | Rh—Ta/ZrO$_2$—SiO$_2$ | 192 | 200 | 0.5 | 80 | 0.059 | 0.079 | 0.612 | 0.075 | 1.339 |
|  | (Rh 0.48, Ta 0.24 g) | 192 | 200 | 0.5 | 80 | 0.039 | 0.140 | 0.602 | 0.094 | 1.164 |
|  | ZrO$_2$/SiO$_2$ = 11.4 wt % | 192 | 190 | 0.5 | 80 | 0.041 | 0.052 | 0.405 | 0.056 | 0.430 |
|  |  | 192 | 210 | 0.5 | 80 | 0.062 | 0.089 | 0.705 | 0.096 | 1.677 |
| 22 | Rh—Ta/ZrO$_2$—SiO$_2$ | 192 | 190 | 0.5 | 80 | 0.036 | 0.073 | 0.722 | 0.113 | 1.744 |
|  | (Rh 0.48 g, Ta 0.40 g) | 192 | 180 | 0.5 | 80 | 0.037 | 0.053 | 0.427 | 0.075 | 0.676 |
|  | ZrO$_2$/SiO$_2$ = 11.4 wt % | | | | | 0.028 | 0.038 | 0.286 | 0.043 | 0.354 |

| Example | Amounts of the products (mmoles/hr) C$_2$ | C$_3$ | C$_4$ | CO$_2$ | CO conversion (%) | CE (%) | Ethanol selectivity (%) | STY |
|---|---|---|---|---|---|---|---|---|
| 19 | 0.036 | 0.039 | trace | 0.021 | 3.6 | 59.5 | 96.0 | 2.7 |
|  | 0.098 | 0.102 | 0.026 | 0.051 | 6.7 | 38.2 | 93.3 | 3.1 |
| 20 | 0.141 | 0.165 | trace | 0.037 | 9.8 | 45.0 | 92.8 | 5.5 |
|  | 0.030 | 0.025 | trace | 0.029 | 3.2 | 52.5 | 82.0 | 1.9 |
| 21 | 0.045 | 0.145 | trace | 0.014 | 6.84 | 45.9 | 76.9 | 3.8 |
|  | 0.034 | 0.116 | trace | 0.017 | 6.33 | 49.6 | 76.6 | 4.1 |
|  | 0.013 | 0.049 | trace | trace | 3.14 | 63.8 | 75.8 | 2.6 |
|  | 0.059 | 0.174 | trace | 0.027 | 8.10 | 44.0 | 76.5 | 4.4 |
| 22 | 0.043 | 0.171 | 0.011 | 0.021 | 8.5 | 43.5 | 78.0 | 4.5 |
|  | 0.018 | 0.097 | trace | 0.020 | 4.3 | 52.8 | 74.5 | 2.8 |
|  | trace | 0.041 | trace | 0.013 | 2.4 | 60.9 | 75.1 | 1.8 |

EXAMPLE 23 AND COMPARATIVE EXAMPLE 5

Ten grams (25 ml) of the catalyst used in Example 20 was packed in a stainless steel pressure reactor lined with titanium (40 mm in diameter and 500 mm in length) and subjected to reducing treatment in a stream of hydrogen (1 atm.) at 350° C. for 5 hours. Using the resulting catalyst, a gaseous mixture of CO and H$_2$ was passed through the catalyst layer and reacted under an elevated pressure. The products at the exit of the reactor were analyzed, and the results are shown in Table 11.

For comparison, a catalyst prepared by depositing rhodium chloride on silica was tested for activity in the reaction of a synthesis gas at low to medium pressures. The results are also shown in Table 11.

TABLE 11

| Catalyst | Example 23 Rh—Re—ZrO₂—SiO₂ | | | | | Comparative Example 5 Rh/SiO₂ | |
|---|---|---|---|---|---|---|---|
| Reaction conditions | | | | | | | |
| Gas pressure (kg/cm²) | 20 | 20 | 20 | 30 | 30 | 20 | 40 |
| SV (hr⁻¹) | 1920 | 3840 | 5760 | 3840 | 5760 | 960 | 960 |
| Temperature (°C.) | 220 | 220 | 220 | 230 | 230 | 292 | 282 |
| CO/H₂ mole ratio | 0.5 | 0.5 | 0.5 | 0.5 | 0.5 | 0.5 | 0.5 |
| Feed (ml/min.) | 800 | 1600 | 2400 | 1600 | 2400 | 800 | 800 |
| Amount of the products (mmoles/hr) | | | | | | | |
| CH₃OH | 4.32 | 16.4 | 20.2 | 39.5 | 45.4 | 0.04 | 0.04 |
| CH₃CHO | trace | trace | trace | trace | trace | 1.59 | 0.87 |
| C₂H₅OH | 2.76 | 12.62 | 13.8 | 25.3 | 26.1 | 0.91 | 0.24 |
| CH₃COOH | 0.27 | 1.00 | 1.23 | 2.57 | 1.88 | trace | trace |
| C₃H₇OH | 0.46 | 1.66 | 1.72 | 3.29 | 3.23 | trace | trace |
| C₄H₉OH | trace | 0.54 | 0.37 | 0.65 | 0.74 | trace | trace |
| C₁ | 1.36 | 5.82 | 8.97 | 12.7 | 16.8 | 18.2 | 3.69 |
| C₂ | 0.21 | 1.02 | 1.77 | 2.41 | 3.01 | 2.70 | 0.89 |
| C₃ | 0.20 | 0.49 | 0.90 | 1.04 | 1.24 | 2.69 | 1.92 |
| C₄ | trace | trace | trace | trace | trace | 0.12 | 1.04 |
| CO₂ | 0.11 | 0.34 | 0.33 | 0.68 | 1.01 | | |
| CO conversion (%) | 2.2 | 4.6 | 3.7 | 9.9 | 7.2 | 3.7 | 1.1 |
| CE (%) | 83.6 | 84.0 | 78.5 | 83.5 | 80.6 | 11.2 | 12.8 |
| STY | 30.5 | 131 | 149 | 283 | 339 | 12 | 5 |

EXAMPLE 24

Twenty grams of silica gel (Davison #57) was fired at 300° C. in vacuum. The fired silica gel was dipped in a solution of 5.3 g of titanium tetraisopropoxide in 100 ml of n-hexane. The n-hexane was evaporated off by a rotary evaporator. The dried product was heat-treated in an electric furnace at 200° C. for 2 hours and then at 500° C. for 2 days. Ten grams of the resulting carrier was dipped in a solution of 1.2 g of rhodium chloride trihydrate and 0.25 g of rhenium chloride in 100 ml of methanol. The methanol was removed under high vacuum.

Ten grams of the product containing rhodium chloride and rhenium chloride deposited thereon was packed into the same reactor as in Example 18, and subjected to reducing treatment in a stream of hydrogen first at 100° C. for 1 hour and then at 300° C. overnight. Using the resulting catalyst, the CO-H₂ reaction was carried out in the same way as in Example 18. The results are shown in Table 12.

TABLE 12

| Catalyst | Example 24 Rh—Re/TiO₂—SiO₂ (Rh 0.48 g, Re 0.128 g) TiO₂/SiO₂ = 15.7 wt % | |
|---|---|---|
| Reaction conditions | | |
| SV (hr⁻¹) | 193 | 978 |
| Temperature (°C.) | 182 | 180 |
| CO/H₂ mole ratio | 0.5 | 0.5 |
| Feed (ml/min.) | 79 | 400 |
| Amounts of the products (mmoles/hr) | | |
| CH₃OH | 0.145 | 0.099 |
| CH₃CHO | 0.055 | 0.066 |
| C₂H₅OH | 1.197 | 1.392 |
| CH₃COOH | 0.053 | 0.015 |
| C₃H₇OH | 0.013 | 0.024 |
| C₁ | 1.301 | 1.406 |
| C₂ | 0.103 | 0.104 |
| C₃ | 0.201 | 0.225 |
| C₄ | 0.111 | 0.130 |
| CO₂ | 0.056 | 0.104 |
| CO conversion (mole %) | 10.1 | 2.3 |
| CE (%) | 51.7 | 51.7 |
| Ethanol selectivity (%) | 85.7 | 89.3 |
| STY | 6.6 | 7.3 |

EXAMPLE 25

Rhodium chloride trihydrate (1.2 g) and 0.2 g of rhenium chloride were dissolved in 100 ml of methanol. A zirconium oxide-silica carrier obtained from 2.3 g of zirconium oxynitrate dihydrate and 10 g of silica gel (Davison #57) by heat decomposition at 500° C. in the air was dipped fully in the resulting solution. The methanol was removed by a rotary evaporator, and 10 g of the resulting product was packed into a flowing-type reactor, and subjected to a reducing treatment using a gaseous mixture of 40 ml/min. of hydrogen and 40 ml/min. of helium at 400° C. for 15 hours.

A gaseous mixture consisting of CO, CO₂ and H₂ was passed through the catalyst layer, and reacted. The amounts of the products yielded per hour were examined, and the results are shown in Table 13.

TABLE 13

| Catalyst | Example 25 Rh—Re/ZrO₂—SiO₂ (Rh 0.48 g, Re 0.10 g) ZrO₂/SiO₂ = 11.4 wt % | |
|---|---|---|
| Temperature (°C.) | 190 | 190 |
| Feed composition (ml/min.) | | |
| CO | 20 | 15 |
| H₂ | 40 | 40 |
| He | 20 | 20 |
| CO₂ | 5 | 5 |
| Amounts of the products (mmoles/hr) | | |
| CH₃OH | 0.030 | 0.028 |
| CH₃CHO | 0.032 | 0.034 |
| C₂H₅OH | 0.397 | 0.388 |
| CH₃COOH | — | 0.005 |
| C₁ | 0.465 | 0.281 |
| C₂ | 0.040 | 0.041 |
| C₃ | 0.042 | 0.032 |
| C₄ | 0.012 | 0.012 |
| CE | 54.3 | 62.4 |

EXAMPLE 26

Five grams of the same catalyst as used in Example 24 was packed in a high-pressure reactor similar to the reactor used in Example 23, and subjected to reducing treatment in a stream of hydrogen (5 Kg/cm², 1,000 ml/min.) at 350° C. for 15 hours. The activity of the treated catalyst in the reaction of a gaseous mixture of CO and H₂ under elevated pressure was tested, and the results are shown in Table 14.

TABLE 14

Some Examples of the Results in a Low-Pressure CO—$H_2$ Conversion by the Fixed-Bed Catalyst. (High Pressure Stainless Steel-Reactor, φ40X500 mm long, plated with Titan Metal)

| Reaction Condition | | | | | Yield of Product[3] (mmole $h^{-1}$) | | | | | | | | | | | CO conversion (%) | C.E.[2] (%) | STY[4] (g/kg) cat/$h^{-1}$ |
|---|---|---|---|---|---|---|---|---|---|---|---|---|---|---|---|---|---|---|
| P (kg/cm²) | T (°C.) | Co/$H_2$ | SV ($h^{-1}$) | Feed[1] (ml/min) | MeOH | AcH | ErOH | AcOH | PrOH | BuOH | $CH_4$ | $C_2$ | $C_3$ | $C_4$ | $CO_2$ | | | |
| 20 | 220 | 0.5 | 800 | 1600 | 2.2 | 1.7 | 12.3 | 1.5 | 0.79 | 0.40 | 2.5 | 0.28 | 0.57 | tr. | 0.14 | 1.7 | 84.5 | 92 |
| 40 | 250 | 0.5 | 12000 | 2400 | 8.2 | 3.5 | 27.8 | 1.9 | 2.3 | 1.4 | 10.5 | 0.90 | 1.1 | tr. | 0.42 | 3.0 | 77.7 | 228 |
| 60 | 260 | 0.5 | 12000 | 2400 | 13.3 | 5.6 | 31.9 | 4.0 | 2.5 | 1.7 | 10.2 | 1.1 | 1.3 | tr. | 0.52 | 3.7 | 81.8 | 300 |

Note:
[1]Feed Gas: CO:$H_2$ = 1:1–2 molar ratio, research grade gas.
[2]C.E. Carbon Efficiency of Oxygenated products in carbon basis (%)
[3]AcH = $CH_3CHO$, AcOH = $CH_3COOH$, PrOH = n-$C_3H_7OH$, BuOH = n-$C_4H_9OH$, $C_2$ = $C_2H_4$ + $C_2H_6$, $C_3$ = $C_3H_6$ + $C_3H_8$, $C_4$ = $C_4H_8$ + $C_4H_{10}$
[4]STY Specific Time Yield of Oxygenated Products, g/kg cat/h.
C.R. Comparative Runs
N.A. Non Analysis

What we claim is:

1. In a process for producing an oxygen-containing hydrocarbon compound having 1 or 2 carbon atoms which comprises reacting a gaseous mixture of a carbon oxide and hydrogen in the presence of a hydrogenation catalyst, the improvement wherein said hydrogenation catalyst is a catalyst composition consisting essentially of
   (i) substantially metallic rhodium;
   (ii) a metal element selected from the group consisting of niobium, tantalum and rhenium;
   (iii) an oxide of a metal selected from the group consisting of zirconium and titanium; and
   (iv) silica.

2. The process of claim 1 wherein said metallic rhodium is formed from a simple salt of rhodium.

3. The process of claim 1 wherein the amount of said metallic rhodium is about 0.0001 to about 50% by weight based on the weight of said catalyst composition.

4. The process of claim 1 wherein the weight ratio of metallic rhodium to said metal element is from 10:1 to 1:10.

5. The process of claim 1 wherein the weight ratio of the metal oxide to silica is from 100:1 to 1:100.

6. The process of claim 1 wherein the amount of silica is about 0.001 to about 99.9% by weight based on the weight of said catalyst composition.

7. The process of claim 1 wherein said reaction is carried out at a temperature of about 50° to about 450° C. and a pressure of about 0.5 to about 350 atmospheres (gauge) at a space velocity of about 10 to about $10^6$ liters/liter.$hr^{-1}$.

8. The process of claim 1 wherein the carbon oxide is carbon monoxide.

9. The process of claim 1 wherein the mole ratio of the carbon oxide to hydrogen is from 20:1 to 1:20.

10. The process of claim 1 wherein said catalyst composition consists of the components (i), (ii), (iii) and (iv).

* * * * *